US006440659B1

(12) United States Patent
Mueckler

(10) Patent No.: US 6,440,659 B1
(45) Date of Patent: Aug. 27, 2002

(54) INHIBITORS OF RETROVIRAL PROTEASE AS INDUCERS OF REVERSIBLE INSULIN RESISTANCE IN VITRO AND IN VIVO

(75) Inventor: Mike Mueckler, Chesterfield, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/838,548

(22) Filed: Apr. 19, 2001

Related U.S. Application Data

(60) Provisional application No. 60/198,524, filed on Apr. 19, 2000.

(51) Int. Cl.$^7$ ............................. C12Q 1/70; C12Q 1/06; G01N 33/53; C12N 5/06

(52) U.S. Cl. ........................... 435/5; 435/39; 435/7.72; 435/325; 435/334; 435/339

(58) Field of Search ........................... 435/5, 39, 325, 435/334, 339, 7.72

(56) References Cited

U.S. PATENT DOCUMENTS 5,985,867 A   11/1999   Rodgers et al. .............. 514/218

OTHER PUBLICATIONS

Behrens, A. et al., Impaired glucose tolerance, beta cell functions and lipid metabolism in HIV patients under treatment with protease inhibitors. AIDS 13:63–70 (1999).
Calderhead, D.M. et al., Insulin Regulation of the Two Glucose Transporters in 3T3–L1 Adipocytes. The Journal of Biological Chemistry 265:13800–13808 (1990).
Carr, A. et al., Pathogenesis of HIV–1–protease inhibitor–associated peripheral lipodystrophy, hyperlipidaemia, and insulin resistance. The Lancet 351:1881–1883 (1998).
Carr, A. et al., Diagnosis, prediction, and natural course of HIV–1 protease–inhibitor–associated lipodystrophy, hyperlipidaemia, and diabetes mellitus: a cohort study. The Lancet 353:2093–2099 (1999).
Carr, A. et al., A syndrome of peripheral lipodystrophy, hyperlipidaemia and insulin resistance in patients receiving HIV protease inhibitors. AIDS 12:51–58 (1998).
Cline, G.W. et al., Impaired Glucose Transport as a Cause of Decreased Insulin–Stimulated Muscle Glycogen Synthesis in Type 2 Diabetes. The New England Journal of Medicine 341:240–246 (1999).
CNN Interactive, New concerns about side effects of AIDS–fighting protease inhibitors, Jun. 30, 1998 (news article).
Erbelding, E.J., Metabolic Complications of Protease Inhibitors: What Have We Learned in the Past Year? The Hopkins HIV Report, http://hopkins–aids.edu/publiations/report/mar99_5.html (Mar. 1999).
Griffin, C., Side Effects of Protease Inhibitors: An Informal Survey. Being Alive Newsletter, http://www.beingalicela.org/news0596/0596protease1.html (May 1996).
James, J.S., Protease Inihibitors; Metabolic Side Effects: Cholesterol, Triglycerides, Blood Sugar, and "Crix Belly". Interview with Lisa Capaldini, M.D.. AIDS Treatment News 277, http://www.immunet.org/immunet/atn.nsf/page/1–277–01 (1997).

(List continued on next page.)

Primary Examiner—Hankyel T. Park
(74) Attorney, Agent, or Firm—Saul Ewing LLP; Alfred W. Zaher; Bruce D. George

(57) ABSTRACT

This invention provides novel assays for measuring the metabolic side-effects of antiretroviral protease inhibitors on the Glut4 glucose transporter. The invention also provides improved methods for developing antiretroviral protease drugs, particularly those used to fight HIV infection. The invention further provides novel models of insulin-resistant glucose transport disease states.

28 Claims, 10 Drawing Sheets

OTHER PUBLICATIONS

Katz, E.B. et al., Cardiac and adipose tissue abnormalities but not diabetes in mice deficiency in GLUT4. Nature 377:151–155 (1995).

Keller, K. et al., Functional Expression of the Human HepG2 and Rat Adipocyte Glucose Transporters in Xenopus Oocytes. The Journal of Biological Chemistry 264:18884–18889 (1989).

Kotler, D.P. and Engelson, E.S., Summary Report, Third International Conference on Nutrition and HIV Infection, Cannes, France—Apr. 22–25, 1999. Medscape HIV/AIDS 5(3) 1999.

Kotler, D.P., Lipodystrophy: Return of the Splitters. Medscape, http://www.medscape.com/medscape/cno/2000/retro/Story.cfm?story_id=1009 (2000).

Kotler, D.P., Coming of Age: Metabolic Complications of Antiretroviral Therapy. Medscape, http://www.medscape.com/medscape/cno/2000/retro/Story.cfm?story_id=1015 (2000).

Mulligan, K. et al., Hyperlipidemia and Insulin Resistance Are Induced by Protease Inhibitors Independent of Changes in Body Composition in Patients With HIV Infection. JAIDS Journal of Acquired Immune Deficiency Syndrome 23:35–43 (2000).

Reaven, G.M., Role Of Insulin Resistance In Human Disease (Syndrome X): An Expanded Definition. Annu. Rev. Med. 44:121–131 (1993).

Safrin, S. and Grunfeld, C., Fat distribution and metabolic changes in patients with HIV infection. AIDS 13:2493–2505 (1999).

Wentworth, J.M., et al. HIV protease inhibitors block human preadipocyte differentiations, but not via the PPARγ/RXR heterodimer. Journal of Endocrinology 164:R7–R10 (2000).

Zhang, B. et al., Inhibition of Adipocyte Differentiations by HIV Protease Inhibitors. The Journal of Clinical Endocrinology & Metabolism 84:4274–4277 (1999).

Abstracts 1–4768, Tutorials T1–T20, Experimental Biology 96™, Washington, DC, Apr. 14–17, 1996.

Murata, H., Hruz, Paul W., and Mueckler, M., *The Mechanism of Insulin Resistance Caused by HIV Protease Inhibitor Therapy, The Journal of Bilogical Chemistry*, vol. 275, No. 27, pp. 20251–20254, Jul. 7, 2000.

INHIBITORS OF RETROVIRAL PROTEASE AS INDUCERS OF REVERSIBLE INSULIN RESISTANCE IN VITRO AND IN VIVO

This application claims priority to U.S. Provisional Application No. 60/198,524, filed Apr. 19, 2000, the entirety of which is incorporated by reference herein.

Pursuant to 35 U.S.C. §202(c), it is acknowledged that the U.S. Government has certain rights in the invention described herein, which was made in part with funds from the National Institutes of Health, Grant No. DK38495.

FIELD OF THE INVENTION

This invention relates to the field of cellular biology and disease states, including HIV infection and diabetes. Specifically, this invention provides novel assays for the effects of antiretroviral protease inhibitors on the Glut4 glucose transporter and a novel in vivo model of insulin-resistant glucose transport disease states.

BACKGROUND OF THE INVENTION

Several publications are referenced in this application in order to more fully describe the state of the art to which this invention pertains. Each of these publications is incorporated by reference herein.

The development of new targets for therapeutic agents for the treatment of HIV infections, as well as powerful combinations of those therapeutic agents has led to what is now commonly referred to as HAART (for highly-active antiretroviral therapies). Among the cornerstones of the therapeutic components of these HAART approaches are the antiretroviral protease inhibitors which have been developed. As part of combination therapies, HIV protease inhibitors play a critical role in suppressing viral titers and increasing CD4+ lymphocyte counts, which can result in significantly reduced mortality among HIV patients.

The human immunodeficiency virus (HIV) genome encodes an aspartyl protease that is required to process its viral precursor polyproteins to their mature forms. This protease activity is essential for the proper formation of infectious HIV virions. The development of a class of specific agents that target the HIV protease was an extraordinary advance in the treatment of HIV infection.

Despite the rapid progress in the treatment of the disease, and the improved prognosis for those infected, it now appears clear that the use of protease inhibitors is associated with potentially serious side effects. In 1997, the FDA issued a Public Health Advisory to healthcare professionals warning that use of protease inhibitors was associated with increases in blood sugar and diabetes. Eighty-three cases had been reported, of which twenty seven required hospitalization. Diabetes cases were associated with use of several available protease inhibitors, including indinavir, nelfinavir, ritonavir, and saquinavir.

Although the mechanisms have not been elucidated, it is clear that protease inhibitor use is linked in some manner to a syndrome of alarming metabolic abnormalities characterized by hypertriglyceridemia, hypercholesterolemia, peripheral fat wasting, central adiposity and hyperglycemia and insulin resistance. The etiology of this metabolic syndrome associated with protease inhibitor use currently remains unknown, but its features are similar to those present in the insulin-resistant state commonly referred to as Syndrome X. Common symptoms of the syndrome include body fat changes including: enlarged dorsicervical fat pads (known as "buffalo hump"); abundance of benign lipomas; deposition/accumulation of fat in the abdomen or viscera (Crix belly); breast hypertrophy; and a characteristic loss of fatty tissue from the face and extremities. Collectively these body fat changes are referred to as lipoatrophy, or more commonly, lipodystrophy. Hyperlipidemia and insulin resistance appear to occur with high prevalence among patients using protease inhibitors, such that increased risk of premature cardiovascular disease and diabetes are relevant issues. The prevalence of lipodystrophy has been reported to be as high as 83% according to one study. Other studies suggested that some of the symptoms may appear to varying degrees in patients not treated with protease inhibitors, or that symptoms vary depending upon which protease inhibitor was used for treatment. Yet other studies revealed possible differences in patients based on age, gender, length of infection and other factors such as change in weight and hemophilia.

Thus, sustained treatment with the currently available antiretroviral protease inhibitors results in at least some, or all, of these metabolic disturbances, particularly those associated with hyperlipidemia and insulin resistance. The long-term, or even near-term, risk to the health of patients, while less than the imminent risk of uncontrolled viral growth, is substantial. The ability to design drugs lacking the undesirable side-effects is widely recognized as a need in the art and would be of great significance in combating HIV and other retroviral diseases. Furthermore, a more detailed understanding of the molecular mechanisms which lead to this metabolic disorder would contribute to the development of novel experimental or in vivo models related to the generalized problem of insulin resistance.

SUMMARY OF THE INVENTION

It has now been discovered in accordance with the present invention that anti-HIV drugs of the protease inhibitor class, including, for example, indinavir, ritonavir and amprenavir, are selective inhibitors of the Glut4 glucose transporter. This discovery enables the development of assays for use in screening of protease inhibitors for this unwanted and undesirable side-effect; in addition, improved procedures for the rational design and testing of antiretroviral protease inhibitors are enabled by this novel method.

The present invention provides novel assays for determining the effect of protease inhibitors on glucose transport activity. The invention also provides methods for screening antiretroviral protease inhibitor drugs for side-effects related to glucose transport in the presence or absence of insulin stimulation. In its most basic and general form, the assay method comprises the steps of; providing glucose transporters of interest in a membrane system; incubating the glucose transporters with a measurable form of glucose or a glucose analog; adding to the incubation mixture a antiretroviral protease inhibitor being screened; optionally, stimulating the glucose uptake of the cells with insulin; and quantifying the glucose transport by determining the difference in the amount of glucose uptake in the presence and in the absence of the protease inhibitor being screened, and optionally, in the presence or absence of insulin, or other glucose transport-altering substances. The invention provides, in one embodiment, that the glucose transporter is a Glut4 isoform. In one basic embodiment the membrane system comprises cells, for example adipocytes, producing a glucose transporter. The invention provides a wide variety of cells for use with the methods.

Also provided in accordance with the present invention is a method for testing a wide variety of antiretroviral protease inhibitors for side-effects on glucose transport. Included among the protease inhibitors and their derivatives to be tested by the method above are various compounds and families of compounds, many of which are already established as inhibitors of aspartyl proteinases.

The invention also provides for a variety of glucose compounds to be used as the detectable glucose. Glucose compounds include glucose, and its analogs, including transportable analogs of glucose.

The invention also provides methods for measuring the side-effects of protease inhibitors on glucose transport in cell-free systems. The advantages of cell-free systems are well known in the art. In the cell-free methods of the invention, the membrane system selected comprises a naturally-derived membrane from cells in certain embodiments, while in others, a noncellular system, for example, artificial membranes or vesicles, is used with the glucose transporter isoforms.

Also provided for use in the methods of the present invention when the membrane system selected is cells, are cells containing one or more expressible nucleic acids encoding one or more glucose transporters. The invention provides that the cellular expression of the glucose transporter is a stable characteristic of the cell line in certain embodiments. In other embodiments, the expression of the glucose transporter is transient. The expressible nucleic acids encode one or more homologous or heterologous glucose transporters of interest. In one embodiment, the cells have a substantially negligible basal level of glucose transport, other than the glucose transport provided by the heterologous glucose transporter.

Also provided in accordance with the present invention are kits for testing protease inhibitors for side-effects involving glucose transport. The utility of such kits is well established. The kits of this invention can include a cell line complete with heterologous glucose transport expression capability, or another membrane system with glucose transporter isoforms, and a detectable glucose compound, such as glucose or a glucose analog. Further included are standards for insulin stimulation, and protease inhibitors for standardizing the inhibition assays.

The invention further provides a method for the rational design of new antiretroviral treatments. The method provides that a candidate drug or lead compound be subjected, in the early stages of the drug development, to assays to measure effects on glucose transport. The assay method comprises the steps of identifying a therapeutic test compound; testing the compound by: determining that it inhibits a retroviral aspartyl protease; using the compound as a protease inhibitor in the screening method described above; assessing the compound for inhibition of glucose transport; and selecting those compounds which inhibit the aspartyl protease and which do not inhibit glucose transport. Candidates of greatest interest for further development are those which maximally inhibit the retroviral protease but do not substantially alter the glucose transport activity in either the presence or absence of insulin stimulation.

Further provided in the invention are methods of cell-free methods of rapidly screening protease inhibitors for specific molecular interactions with glucose transporters. Such specific molecular interactions are an indication of potential inhibition or undesirable side-effects of protease inhibitors. These methods provide for labeled glucose transporters and or labeled protease inhibitors. The invention provides for measuring the specific molecular interactions between either a membrane-associated or solubilized glucose transporter and a protease inhibitor.

Also provided in accordance with the present invention is a method of screening factors, compounds or conditions which alter reversible insulin-resistant glucose transport. Compounds identified by such a method would be excellent candidates for treating disease conditions comprising insulin resistance. The method comprises the steps of: providing a cell line producing one or more glucose transporters; incubating the cells with a detectable glucose or glucose analog in the presence of an inhibitor known to specifically inhibit the glucose transporter isoform of interest; including a compound or condition whose effects on reversing the inhibition are to be tested; and quantifying the reversal of glucose transport inhibition. Also provided are such assays in either the presence or absence of insulin or other glucose transport-altering substances.

Other features and advantages of the present invention will be understood by reference to the detailed description of the invention and examples that follow.

BRIEF DESCRIPTION OF THE DRAWINGS

FIG. 1. The effect of HIV protease inhibitors on glucose uptake in 3T3-L1 adipocytes.

FIG. 2. Indinavir does not affect insulin signaling or glucose transporter translocation.

FIG. 3. Inhibition of glucose uptake in *X. laevis* oocytes by HIV protease inhibitors.

FIG. 4. Effect of acute indinavir administration on glucose tolerance in rats.

Jugular vein and carotid artery catheters were inserted, at least 4 days prior to each experiment, into 200–400 gm male Wistar rats under methohexital anesthesia. Following an overnight fast, rats were infused with insulin (40 mU/kg/min) and 50% dextrose through the venous catheter. Blood was sampled every 5–10 minutes through the arterial catheter and serum glucose concentrations were determined. The glucose infusion rate (GIR) space was adjusted to maintain glucose levels of 100–110 mg/dl. Solid arrows represent the start of a continuous infusion of water containing indinavir through the intravenous line. Open arrows represent the discontinuation of the indinavir infusion.

Figure 5A:
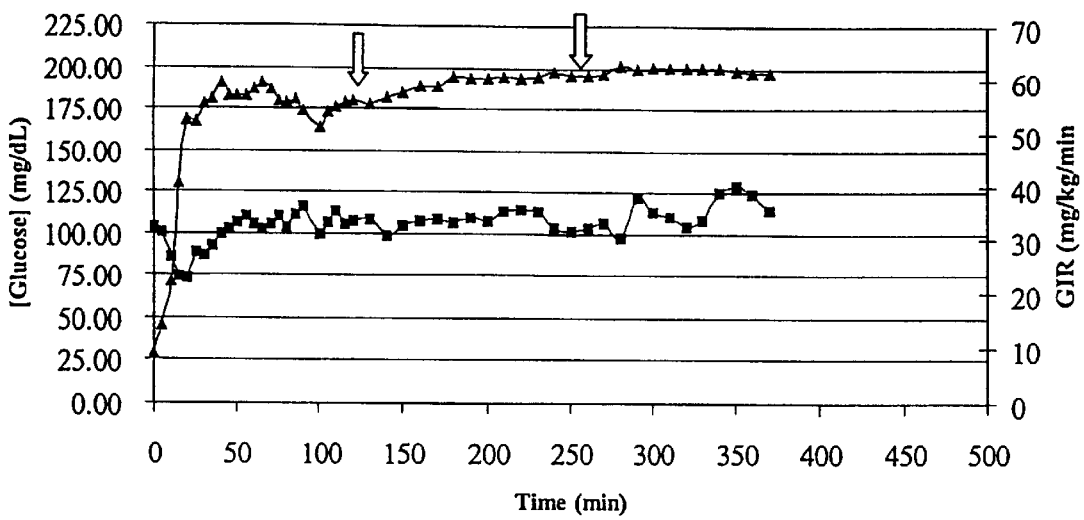
FIG. 5. Effect of acute intravenous administration of indinavir on peripheral insulin sensitivity in rats.

FIG. 5A: Control Experiment (no indinavir), FIG. 5B: 0.3 mg/kg/min indinavir, FIG. 5C: 0.5 mg/kg/min indinavir.

Figure 6:
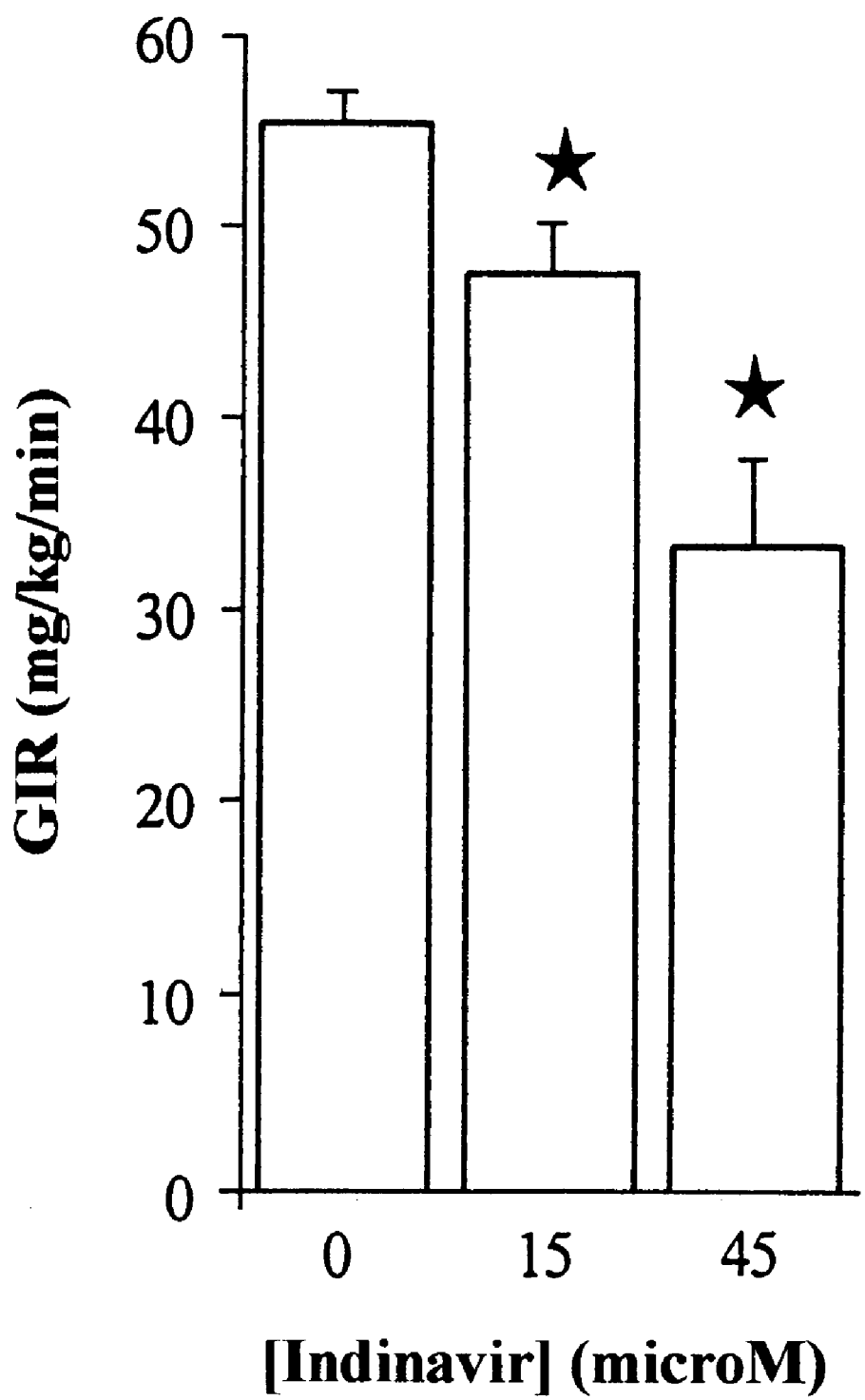

FIG. 6. Reduction in peripheral insulin sensitivity induced by acute intravenous indinavir administration in rats.

Male Wistar rats weighing 200–300 gm were catheterized as described in FIG. 5. Following an overnight fast, a continuous infusion of water containing 0, 0.3 or 0.5 mg/kg/min indinavir was started through the venous catheter. After 30 minutes, insulin (40 mU/kg/min) and 50% dextrose were added to the intravenous infusion. Blood was sampled through the arterial line every 5 min and the dextrose infusion rate was adjusted to maintain plasma glucose levels between 105–115 mg/dL. GIR represents the mean glucose infusion rate during the final 30 minutes of each 2 hour clamp experiment. Results represent the mean±SEM from 3–5 rats per group. [* indicates P<0.5]

DETAILED DESCRIPTION OF THE INVENTION

1. Definitions

Various terms relating to the biological molecules of the present invention are used hereinabove and also throughout the specifications and claims. Certain aspects of the present invention employ conventional molecular biology, microbiology, and recombinant DNA techniques that are well known in the art. See, e.g., Sambrook et al., "Molecular Cloning: A Laboratory Manual (1989); or "Current Protocols in Molecular Biology", eds. Frederick M. Ausubel et al., John Wiley & Sons, 1999. If appearing herein, the following terms have the definitions set out below.

With reference to nucleic acid molecules, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to proteins or peptides, the term "isolated protein (or peptide)" or "isolated and purified protein (or peptide)" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially the same" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservatively substituted amino acids in the encoded polypeptide. With reference to amino acid sequences, the term "substantially the same" refers generally to conservative substitutions and/or variations in regions of the polypeptide not involved in the In determination of structure or function.

A "coding sequence" or "coding region" refers to a nucleic acid molecule having sequence information necessary to produce a gene product, when the sequence is expressed.

As used herein a "heterologous" protein is a protein produced by an organism that is not the wild-type source of that protein. For example, Xenopus cells which have been genetically modified to produce a glucose transporter from rat nucleic acids are producing a heterologous glucose transporter. A heterologous protein is non native or exogenous to the organism producing it.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Where used herein "retroviral protease" refers to the major aspartyl protease common to retroviruses, such as HIV. The retroviral proteases are known to be important to the life-cycle of retroviruses, and have become an important therapeutic target for new drugs.

The term "protease inhibitor" refers to a compound which inhibits the proteolytic action of a proteolytic enzyme. The inhibition may be through a variety of physical and chemical mechanisms, depending the type and structure of the active site of the protease.

The term "antiretroviral" generally refers to a class of drugs used to therapeutically treat infections with retroviruses. The term is also sometimes used herein to refer the properties of a protease inhibitor; i.e. the "antiretroviral properties" of a particular inhibitor are those properties which make it particularly inhibitory to the life cycle of a retrovirus.

The term "antiretroviral protease inhibitor" refers specifically to that subclass of the larger group of protease inhibitors which have activity against retroviral proteases, particularly the proteases of medically significant retroviruses of man and animals. The term as used herein sometimes refers more specifically to a group of protease inhibitors which inhibit the aspartyl protease of HIV.

The term "glucose analog" refers to derivatives of the glucose molecule. Glucose analogs include naturally occurring molecules, and synthetic derivatives. In general the term includes both transportable and nontransportable analogs. A glucose analog may include labels, as with fluorescent glucose analogs, or isotopically labeled glucose analogs.

Where used herein the term "glucose compound" refers to glucose itself, or any glucose analog. The term is often used in the sense of a "detectable glucose compound" or a "detectable glucose" which includes any glucose or glucose analog which can be detected by chemical, enzymatic, physical or other means of detection.

The term "glucose transport-altering substance" as used herein includes hormones, such as insulin, synthetic hormones, hormone analogs, drugs which alter glucose transport, inhibitors, or any compound know to alter the transport of glucose. The term "alteration" or "altering" of glucose transport includes both stimulating and inhibiting alterations, or increases or decreased in glucose transport across a membrane.

Where used herein, the term "molecular interactions" or "physical interaction" broadly refers to the relationship between two molecules, and includes, for example, interactions such as hydrophobic interactions, ionic interactions, hydrophillic interactions, such as water structure, Van der Waal's interactions, covalent interactions. Also included within the meaning of the term are more complex "biological" interactions such as binding site interactions, which typically represent the collective sum of numerous smaller physical and chemical interactions of one or more types, including hydrogen bonding and other transient or statistical interactions of atoms and molecules.

2. Description

The undesired side-effects of anti-HIV protease inhibitors have come to be recognized as a syndrome of metabolic disorders often referred to collectively as lipodystrophy. In the present invention, a selective inhibitory action of these protease inhibitors on the Glut4 glucose transporter isoform, but not on the Glut1 isoform, is an important and novel finding. This finding leads to several useful applications in the screening and rational design of antiretroviral protease inhibitors. In addition, the discovery of selective, reversible, insulin-resistant glucose transport allows for methods to screen drug candidates and factors affecting such transport. Such drugs are needed for the treatment of insulin-resistant disease conditions.

In accordance with the present invention, a method is provided for the screening of protease inhibitors for metabolic side-effects. The method comprises the following steps: providing one or more glucose transporter isoforms in a membrane system; incubating the glucose transporters with a detectable glucose or glucose analog; adding a protease inhibitor of interest; determining activity of the glucose transporter by measuring an amount of glucose transported; and quantifying the metabolic side-effects of the protease inhibitor as a function of the activity of the glucose transporter in the presence of the protease inhibitor compared to that in the absence of the protease inhibitor.

In one embodiment, the membrane system comprises intact cells. The cells may be primary cells or cell cultures. The cells may originate from different tissues known to possess glucose transporter activity. Such tissues include, but are not limited to, adipocytes, kidney cells, cardiac cells, skeletal muscle cells, liver cells, neuronal cells and brain cells. In another embodiment tissues are from rapidly dividing cells, cell-lines or cell populations such as tumor cells, ascites cells, cancerous cells, or transformed cells.

In another embodiment cells are genetically modified or engineered for expression or over-expression of a gene or cDNA. In a preferred embodiment the gene or cDNA encode glucose transporter isoform from a gene or cDNA encoding a glucose transporter.

In another embodiment, cells which have a very low amount of basal glucose transport, such as Xenopus oocytes, are used to transiently express a glucose transporter protein of interest from a nucleic acid encoding the glucose transporter protein.

In one embodiment, the invention provides cells capable of expressing a gene, cDNA, or mRNA encoding one or more glucose transporters. The glucose transporter expressed comprises one or more specific glucose transporter isoforms of interest. In one embodiment, the glucose transporters are expressed transiently; in another embodiment they are expressed in stable fashion. In a preferred embodiment, the glucose transporter is heterologous to the cell line and glucose transport through the heterologous transporter is readily distinguished from the cell's basal level of glucose transport.

The expression of the glucose transporter may be in *Xenopus laevis* oocytes or other cells such as yeast cells (e.g. *Saccharomyces cerevisiae*), insect cells, mouse cells, rat cells, rabbit cells, chimpanzee cells, human cells, or other eukaryotic cells capable of expressing a homologous or heterologous glucose transporter. Prokaryotic cells are also contemplated for use with the methods of this invention. Proper expression of eukaryotic transport proteins in prokaryotes is known in the art. Cells such as *E. coli* are useful in this respect.

In another embodiment, the expression is transient and may be mediated through means such as are known to those skilled in the art, for example, by the microinjection of mRNA molecules encoding one or more glucose transport isoforms of interest. Other methods to generate transient expression of a nucleic acid molecule include, for example, ballistic methods, transient transfection and electroporation.

In a preferred embodiment, the mRNA corresponds to a DNA sequence which is manipulated such that its coding sequence is optimized for expression, according to the codon usage preference tables for the organism in which the mRNA is expressed. The mRNA can be isolated from a biological source or generated by in vitro transcription of a glucose transporter-encoding DNA, methods for both of which are well understood by those skilled in the art.

Glucose transporter-encoding DNAs are known in the art. A table of such sequences is provided below and each of the sequences is readily available in public databases such as GenBank.

| Identified GLUT Sequences and Accession Numbers | | | | | | | | | |
|---|---|---|---|---|---|---|---|---|---|
| Transporter | Human | Mouse | Rat | Chicken | Pig | Trout | Cannis | Carp | Drosphilia |
| | | | | | | | | Rabbit | Bovine |
| GLUT1 | NM006516 K03195 | X69697 M23384 | M13979 | L07300 | X17058 | AF247728 | | AF247730 M21747 | AF064703 448 M60448 |
| GLUT2 | NM00340 XM003153 J03810 | M22998 X16986 X15684 | NM_012879 J03145 | Z22932 | | AF321816 | | | |
| GLUT3 | NM006931 XM006927 M20681 | NM011401 X61093 X69698 M75135 | NM_017102 D13962 | M37785 | L39214 | | L35267 | | |
| GLUT4 | NM001042 XM008339 M20747 | NM009204 BB004644 AB008453 | NM_012751 D28561 M25482 X14771 J04524 | | | AF247395 | | | |
| GLUT5 | NM003039 XM001557 M55531 | NM019741 | D13871 | | | | | | |
| GLUT8 | NM04580 XM011828 Y17801 | NM_019488 AF232061 Y17802 | AJ245935 AB033418 | | | | | | |
| GLUT9 | NM020041 XM003589 AF210317 | | | | | | | | |
| GLUT10 | NM030777 NM030807 | | | | | | | | |
| GLUT11 | NM017585 XM011837 | | | | | | | | |

In other embodiments, the expression of the glucose transporter isoforms of interest is accomplished through the use of genetic elements integrated into the organism's genome or into a stable extra chromosomal element. In these embodiments, it may be desirable to "knock-out" any endogenous basal glucose transporters, such that the heterologous glucose transporter isoforms are the sole or substantially dominant source of facilitated glucose transport. This allows the straightforward measurement or determination of side-effects of added protease inhibitors in the relative absence of background noise. Such "knock-out" mutants are well known in yeast and in other systems, and numerous strategies exist for the generation of such cell lines; combined with stable expression, they allow for routine and standardized assays, and may offer certain advantages over transient expression methods.

In another embodiment, the membrane system comprises membranes other than those in whole cells. Examples of membrane system for use with transmembrane proteins are known to those skilled in the art. Typically such membrane systems comprise phospholipid or other bipolar lipids which provide both hydrophobic and hydrophillic properties. Examples of such systems include cell membranes, cell ghosts, erythrocyte ghosts, membrane-derived vesicles, lipid-containing vesicles, artificial membranes, lipid-containing monolayers, black lipid membranes, reconstituted membranes, hybrid bilayer membranes, supported bilayer membranes, phospholipid-containing membranes or lipid-containing micelles.

In one of its aspects, the method involves a detectable glucose. In one embodiment, the detectable glucose is isotopically labeled. Isotopes, such as those of carbon, iodine, fluorine, and hydrogen may be used for labeling the glucose molecules of the present invention. Detection of such isotopically labeled glucose molecules is known in the art and is accomplished by measuring radioactive decay or mass differences, depending on the type of isotope used. Nuclear magnetic resonance, such as in vivo NMR can be used to measured isotopically-labeled glucose.

The glucose compound is typically a glucose or a glucose analog. Glucose analogs include, for example, methyl glucose, a-methyl glucose, 3-O-methyl glucose, deoxyglucose, 2-deoxyglucose, fluorodeoxyglucose, 2-fluoro-2-deoxy-D-glucose, 3-fluoro-3-deoxy-D-glucose, 2-[N-(7-nitrobenz-2-oxa-1,3-diazol-4-yl)amino]-2-deoxyglucose (2-NBDG), and other transportable glucose analogs. Transportable analogs are preferred for most applications, but nontransportable analogs may be used in certain embodiments. The detectable analogs include radiolabeled molecules, those molecules detectable by emitting energy at specific wavelengths, those molecules detectable by absorbing energy at specific wavelengths, and molecules with detectable mass or atomic differences.

In another embodiment, the glucose is detected via interaction with soluble or immobilized enzyme, one or more substrates or resultant reactants of which are measured, for example electrochemically or optically. In other embodiments the glucose is detectable through other means such as are known to those skilled in the art, for example, an appropriately "labeled" glucose compound may be detectable through optical methods, such as photometric means, fluorometric means, spectroscopic means, or calorimetric means. Alternative means for detecting a glucose compound include, but are not limited to, isotopic means, electrochemical means, or immunologic means. Infrared or near-infrared radiation spectroscopy, impedance methods, including radiowave impedance, and polarized light rotation are further methods which may be used for measuring glucose compounds in specific embodiments. Instruments for detecting molecules by such means are well known in the art. For example, samples may be placed in commercially available glucometer systems, according to the manufacturer's instructions. The foregoing are meant to be illustrative of, and not limiting as to, the methods of detection.

In some embodiments the glucose compound molecule may be a transportable analog or substituted molecule wherein the detectability of the transportable molecular entity may be provided by a nonglucose portion of molecule, and detection is by any means known in the art, such as, but not limited to those enumerated above.

Another aspect of the methods of the present invention involves the use of protease inhibitors, particularly antiretroviral protease inhibitors, for screening for metabolic side-effects, or for use as selective inhibitors of glucose transporter isoforms. Such protease inhibitors may be approved or experimental drugs, drug candidates, or lead compounds in drug discovery efforts. Other embodiments include the targets of rational drug design and/or the products of combinatorial chemistry directed at, for example, antiretroviral drug development.

In one embodiment, the protease inhibitors are antiviral and more specifically antiretroviral therapeutic agents. In some embodiments the protease inhibitors comprise therapeutic cocktails, mixtures or combinations of antiviral compounds. In other embodiments, the protease inhibitors are cruder extracts in various stages of purification or characterization, or pure compounds, such as, but not limited to: peptidomimetic substrates; peptidomimetic substrate analogs or derivatives; aspartyl protease inhibitors; indazole- or other derivatives of cyclic ureas; sulfonamides; derivatives of 2,4-diamino-3-hydroxycarboxylic acid; derivatives of phosphoric acid; and/or the aspartyl proteinase inhibitors described in U.S. Pat. No. 5,945,413, and the like.

In one embodiment of the protease inhibitor screening method, protease inhibitors are added to the assays at various time points before during or after the initiation of glucose transport measurement or before, during or after insulin stimulation to determine the kinetic properties of the protease inhibitor's effect on glucose transport. It is well known in the art that determining the kinetic properties of a molecular interaction can lead to deeper understanding of the mechanisms, which will ultimately lead to the identification or development of compounds with improved protease inhibitor effects and eliminated or optimized ratio of protease inhibitor effect to metabolic side-effects. Such kinetic assays are valuable in understanding the nature of the interaction of each protease inhibitor tested with the glucose transport apparatus.

The invention also provides for glucose transport altering substances to be added to the assays. Glucose transport altering substances include hormones, such as insulin, synthetic hormones, and hormone analogs, as well as other compounds, for example, peptides and drugs, which are capable of altering glucose transport in cells. Glucose transport altering substances may have their action directly on the glucose transporters of the invention, or where intact cells are used, the glucose transport altering substances may operate through biological signaling cascades and may involve secondary message compounds directly or indirectly.

In another aspect of the present invention, a new and useful method for the rational design of antiretroviral protease inhibitors is provided. The method comprises the following steps: 1) identifying a drug candidate or lead compound; 2) testing the compound to determine that it is effective in inhibiting the aspartyl protease of the HIV or other retroviruses; 3) further testing the compound for inhibition in glucose transport assays; 4) assessing the compound's effects on glucose transport; and 5) selecting compounds which are effective at inhibiting the aspartyl protease in step 2) and possess minimal undesirable side-effects in step 3). Most desirable are those compounds which further satisfy all other clinical, toxicological and pharmacological requirements for a new drug.

One useful advantage of this method is that by incorporating, from the earliest design stages, an assay for the unwanted side-effects, expensive and time-consuming efforts which lead to dead-end compounds can be minimized. Since the particular undesirable metabolic side-effects of the protease inhibitors are already recognized as a substantial problem, this method of rational design incorporating the strategy of testing for a known metabolic side-effect early on in the design process, will ultimately lead to more efficient drug development programs for retroviral diseases.

It is anticipated that in various embodiments, such a rational drug design method could include lead compounds which can be detected or identified by a variety of screening methods. One embodiment employs high-throughput screening, which has proven useful for identifying compounds with promise as drug candidates. Another embodiment uses combinatorial chemistry, which has also proven itself as a strategy for generating lead compounds. Other strategies contemplated for use with this invention include shotgun approaches and rational screening programs. In another embodiment the lead compounds are generated through ethnobotanical screening programs and the like, whereby antiviral compounds from plants and other natural sources are also contemplated as sources of drug candidates for the method of the present invention.

The testing of drug candidates for effects on glucose transport employs the method as described above in one embodiment. In another embodiment, such a method may be simplified for screening purposes to measuring a specific molecular or physical interaction between a membrane-free or membrane-bound glucose transporter and a protease inhibitor. Such interactions between a transmembrane transporter and an inhibitor are known in the art. Analogous molecular interactions may occur between enzymes and inhibitors. Some examples of these interactions include covalent modification, hydrophobic interaction, ionic interactions, zwitterionic or amphiphillic interactions, hydrophillic interaction, site-specific binding, occlusion of an active site, and blocked access to a translocation channel. Although the exact mechanism of the molecular interactions remain uncertain, it is clear that these interactions occur and that they are not nonspecific, being properties of particular molecules and not others. In the present invention, it has been shown that the antiretroviral protease inhibitors selectively inhibit the Glut4 but not the Glut1 isoforms of the glucose transporter.

The simplified method of quickly measuring a molecular or physical interaction between the glucose transporter and a protease inhibitor typically comprises a glucose transporter in an artificial system. Artificial systems such as lipid vesicles, micelles, monolayers, or artificial membranes containing glucose transporter molecules are contemplated herein. The glucose transporter can also be solubilized in a manner which allows interaction with the protease inhibitors to occur. Solubilized transporters are known in the art, as are methods for solubilizing membrane proteins, such as glucose transporters.

Such simplified assays allow miniaturization and automation. These in vitro model assays can be conducted as part of high throughput screening program, with the more traditional cell-based glucose transport assay as a follow-up. Detection of a potentially inhibitory interaction between a glucose transporter and a protease inhibitor in such an assay could be by any of the methods well-known and widely-used in the art, for example by the use of fluorescently-labeled glucose transporter and the measurement of quenching of the fluorescent signal during interaction with an appropriate inhibitor. Other methods of measuring or detecting molecular interactions between such molecules as membrane components and soluble components are known in the art and may be used in conjunction with the instant invention. For example, either the glucose transporter or the protease inhibitor can be labeled with a photolabile component which when exposed to a particular wavelength light will result in a chemical reaction, for example, the covalent binding of portions of the interacting molecules which are within a certain proximity. This covalent interaction allows the specific portions of interacting molecules to be identified, by various means, such as mass spectroscopy, fluorescent detection, spectroscopic means, photometric means, and separation means such as chromatographic means. These covalently modified portions can then be identified and the portions of the molecules which were physically interacting can be deduced from the data.

Derivatization of inhibitors with fluorescent, isotopic or photolabile labels can be used to provide a direct measurement of inhibitor binding to or interaction with the glucose transporter.

The glucose transporters of the molecular interaction method above are obtained from biological sources by extraction and or purification by means known in the art. Other methods for obtaining glucose transporter molecules for measuring molecular interactions with protease inhibitors include in vitro translation from glucose transporter-encoding mRNAs, or combined in vitro transcription/translation from glucose transporter-encoding DNA molecules. Synthetic glucose transporter molecules can be made from known amino acid sequences, or sequences altered therefrom, for use in the molecular interaction method. Additionally, in one embodiment, portions of glucose transporters may be synthesized or generated from biologically derived glucose transporters for efforts to to determine particular molecular domains of the glucose transporters involved in molecular interaction with protease inhibitors. The glucose transporters obtained as described herein can also be used in the cell-free methods of measuring glucose transport as described herein, including by incorporation into lipid vesicles, bilayers and the like.

In a preferred embodiment, the most promising drug candidates for preclinical studies, as well as further toxicological, pharmacological and clinical studies are those compounds which are initially selected by a high throughput screening method for the properties of (1) protease inhibition and (2) no significant interaction with glucose transporter, and optionally (3) which continue to show no significant effect on glucose transport by the transport method described above. Such drug candidates will certainly yield the most beneficial results throughout the further steps of approval as new drugs.

In a different aspect of the instant invention, screening assays are provided to identify target therapeutic compounds which can restore insulin-dependent glucose transport. For such assays, a model is used wherein a glucose transporter is produced by a cell. The method comprises the steps of providing a reaction medium comprising cells that produce one or more glucose transporters, a quantity of an inhibitor of retroviral protease that reversibly inhibits insulin-dependent glucose transport of the transporter, a quantity of insulin, and a glucose compound; measuring the amount of the glucose compound transported into the cells under preestablished conditions for a preestablished time period; adding the test compound to the reaction medium; measuring the amount of the glucose compound transported into the cells under preestablished conditions for a preestablished time period; and determining the difference between the amount of glucose transported into the cells after addition of the test compound and the amount of glucose transported into the cells before addition of the test compound, an increase in the amount of glucose transported into the cells after addition of the test compound being indicative that the test compound is capable of reversing the inhibition of the insulin-dependent glucose transport caused by the protease inhibitor.

The method provides for the screening of drugs which act directly at the site of reversible insulin resistance, i.e. compounds which specifically reverse-insensitivity of the glucose transporter, particularly the Glut4 isoform. Compounds which reverse the insulin resistance may also work at other, secondary, locations remote to the glucose transporter since these assays are typically performed in intact cells. In a cell-free mode, primarily compounds are detected in the screening method which act more directly on the glucose transporter. The method is particularly valuable as part of a program of developing new drug candidates for reversing insulin resistance. Following the screening assay, candidate compounds are able to be tested in in vivo models and then sent to preclinical and clinical studies.

In one embodiment, the invention provides cells that are specifically engineered to have a dominant glucose transporter as an reversibly-inhibitable insulin-sensitive glucose transporter. Such cells produce a glucose transporter by expressing the gene product of a nucleic acid molecule which encodes a glucose transporter. In a preferred embodiment, the glucose transporter is known to be susceptible to inhibition by antiretroviral protease inhibitors. In one embodiment the glucose transporter is a Glut4 isoform.

In another embodiment, in vivo methods are provided to assay target therapeutic compounds for the reversal of protease inhibitor induced insulin-resistance using the euglycemic-hyperinsulinemic clamp procedure. This method is particularly useful for assaying compounds which have been promising in the in vitro methods as described above.

The following examples are provided to describe the invention in greater detail; they are intended to illustrate, not to limit, the invention.

EXAMPLE I

The Mechanism of Insulin Resistance Caused by HIV Protease Inhibitor Therapy

Methods

Materials.

Indinavir, ritonavir, and amprenavir were obtained from Merck, Abbott, and Glaxo Wellcome, respectively. *Xenopus laevis* imported African frogs were purchased from Xenopus Express (Homasassa, Fla.). All other reagents unless otherwise specified were obtained from Sigma.

Cell Culture of 3T3-L1 Adipocytes

3T3-L1 fibroblasts obtained from the American Type Culture Collection were grown to confluence and 48 h later subjected to the differentiation protocol described previously (Tordjman et al. 1989). Mature 3T3-L1 adipocytes were maintained in DMEM supplemented with 10% fetal bovine serum and used 10 to 15 d post-differentiation.

2-Deoxyglucose Uptake Measurements in 3T3-L1 Adipocytes

3T3-L1 adipocytes grown in 3.5 cm dishes were serum-starved for at least 3 hours and then washed three times with Krebs-Ringer phosphate buffer. [$^3$H]-2-deoxyglucose uptake (50 $\mu$M cold 2-deoxyglucose) was measured in Krebs-Ringer phosphate buffer as described previously (Tordjman et al. 1989) for 6 min at 37° C. under basal and insulin-stimulated conditions (1 $\mu$M insulin for 20 min). Where so indicated, HIV protease inhibitors (indinavir, ritonavir, or amprenavir) were added to the cells at designated concentrations 6 minutes prior to the assay. Stock solutions of indinavir and amprenavir were made in water. Ritonavir was dissolved in ethanol. When adding ritonavir to cells, the final concentration of ethanol was less than 0.5%. Non-specific uptake was measured in the presence of 20 $\mu$M cytochalasin B and subtracted from the experimental values.

Subcellular Fractionation of 3T3-L1 Adipocytes

3T3-L1 adipocytes were grown in 10 cm$^2$ dishes and incubated at 37° C. for 4 hours in serum-free DMEM in the absence or presence of 100 $\mu$M indinavir. After treatment with or without insulin (1 $\mu$M for 20 min), the cells were scraped in ice-cold HES buffer (20 mM HEPES, pH 7.4, 255 mM sucrose, and 1 mM EDTA) supplemented with 100 mM sodium fluoride, 10 mM sodium pyrophosphate, 1 mM sodium vanadate, and general protease inhibitors (1 $\mu$g/ml leupeptin, 1 $\mu$g/ml antipain, 5 $\mu$g/ml trypsin inhibitor, 1 $\mu$g/ml chymostatin, 1 $\mu$g/ml pepstatin A, and 0.5 mM phenylmethylsulfonyl fluoride). After homogenization through 11 passes in a Yamato LSC homogenizer (1200 rpm) at 4° C., subcellular fractionation by differential centrifugation was performed as described previously (Piper et al., 1991).

Immunoblot Analysis

3T3-L1 adipocyte fractions were subjected to SDS-PAGE and transferred to nitrocellulose. Glut1 and Glut4 transporters were detected using polyclonal antibodies raised against peptides corresponding to the carboxy-terminal 16 residues of the respective transporter isoform. The autoradiographic signals were quantified by using a phosphorimager (Molecular Dynamics.). Phosphotyrosine-containing proteins were detected using the monoclonal PY-20 antibody (Transduction Laboratories). Phospho-Akt specific antibodies (New England Biolabs) were used to detect Akt phosphorylated at threonine 308 and serine 473.

Confocal Immunofluorescence Microscopy

3T3-L1 adipocytes were grown on No. 1 glass coverslips. Cells were incubated in the absence or presence of 100 $\mu$M indinavir as described above for subcellular fractionation. After treatment with or without insulin (1 $\mu$M for 20 minutes), whole cells were fixed immediately in 4% paraformaldehyde and permeabilized using methanol. PM sheets adherent to the coverslip were prepared by gentle sonication as described previously (Robinson et al., 1992) and subsequently fixed using 4% paraformaldehyde. Glut1 and Glut4 subcellular distributions in the prepared coverslips were visualized by indirect immunofluorescence microscopy using isoform-specific polyclonal antibodies essentially as described previously (Robinson et al., supra). Images were taken using a Bio-Rad MRC-1024 laser scanning confocal microscope.

2-Deoxyglucose Uptake Measurements in Xenopus oocytes

*Xenopus laevis* oocytes were prepared and injected as described previously (Keller et al., 1989) with 50 ng of either Glut1 or Glut4 mRNA synthesized in vitro (Megascript RNA synthesis kit, Ambion). After a three day incubation in Barth=s saline containing albumin at 18° C., groups of 15–20 oocytes were washed and [$^3$H]-2-deoxyglucose (50 $\mu$M) uptake measurements were performed in Barth's saline at 22° C. for 30 minutes. HIV protease inhibitors (indinavir, amprenavir, or ritonavir) were added to the assay mixture immediately prior to the uptake measurement.

Results

2-Deoxyglucose Uptake Measurements in 3T3-L1 Adipocytes

Figure 1A:
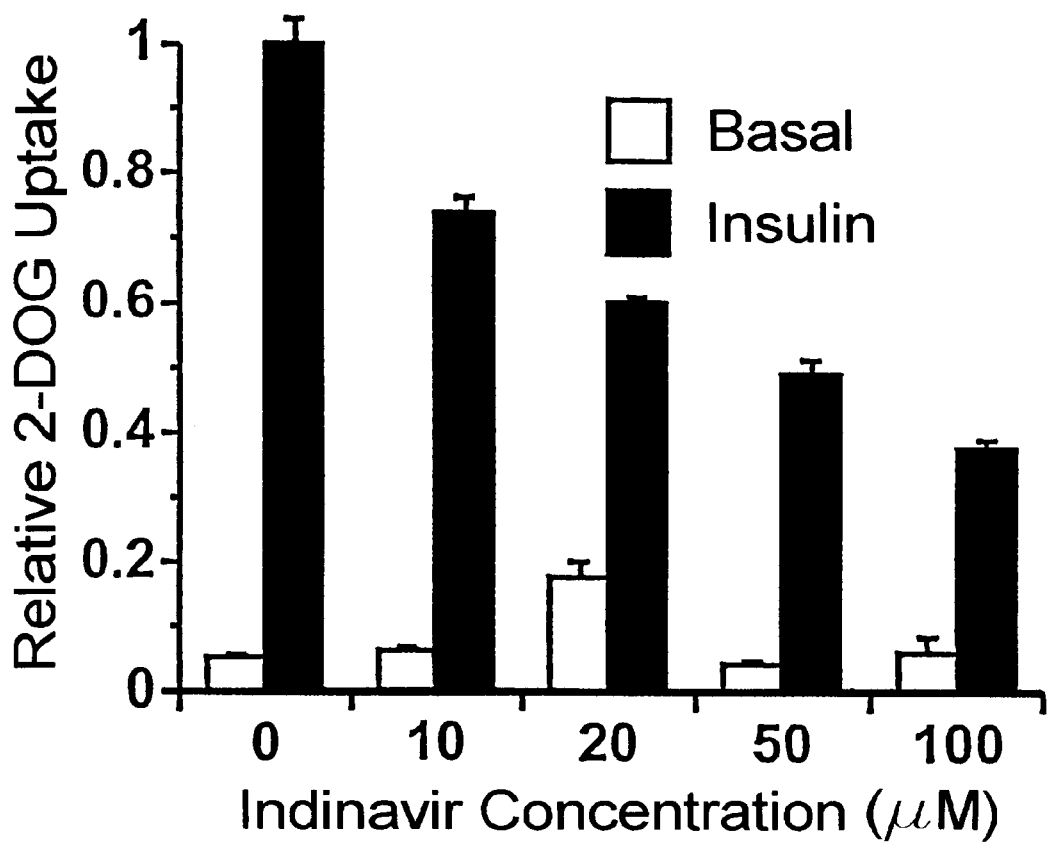
FIG. 1A. Cells were incubated at 37° C. in the presence of indinavir sulfate, added to final concentrations of 10, 20, 50, or 100 $\mu$M (as indicated on the X-axis), for 6 min prior to the glucose uptake assay. [$^3$H]-2-deoxyglucose uptake was measured for 6 min under basal and insulin-stimulated conditions (incubation with 1 $\mu$M insulin for 20 min prior to assay). Results from three experiments were normalized to the value obtained from insulin-stimulated control cells and are shown as the mean±S.E. (n=6).
Figure 1B:
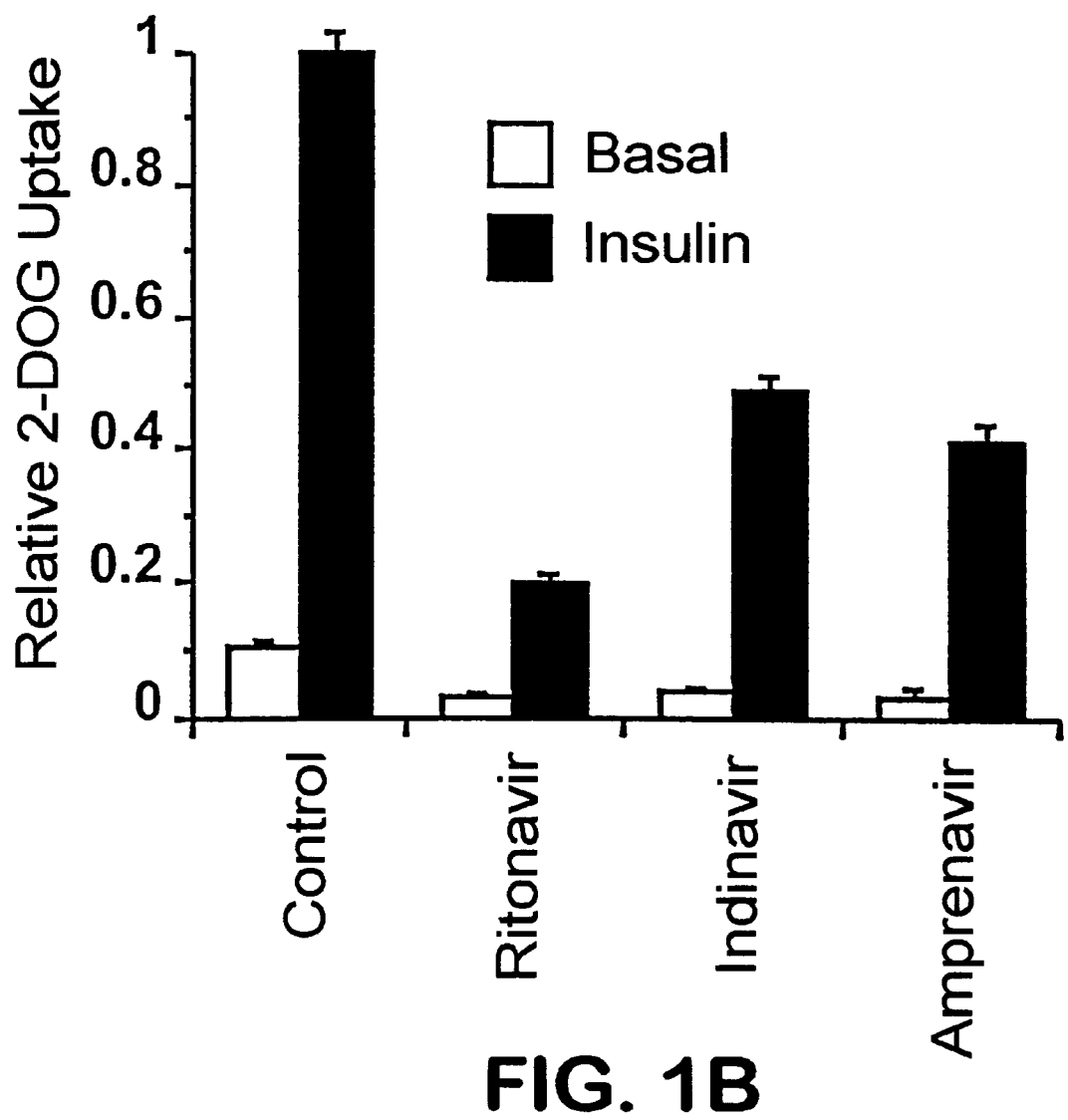
FIG. 1B. 3T3-L1 adipocytes were treated with either no protease inhibitor (Control), or with ritonavir, indinavir, or amprenavir, at 50 $\mu$M. [$^3$H]-2-deoxyglucose uptake was measured as described above. Results were normalized to the value obtained from insulin-stimulated control cells and are shown as the mean±S.E. (n=3).

When 3T3-L1 adipocytes were treated with indinavir, a statistically significant dose-dependent decrease in insulin-stimulated glucose uptake was inhibited 63% at the maximum concentration of indinavir tested (100 $\mu$M; FIG. 1A). At 10 $\mu$M, indinavir inhibited insulin-stimulated glucose uptake by 26% (p<0.0001). Basal glucose uptake was largely unaffected by indinavir, although at 20 $\mu$M indinavir, a modest increase was reproducibly observed. The inhibitory effect of indinavir on insulin-stimulated glucose uptake was very rapid, as the drug was added to the cells only 6 minutes prior to the uptake assay. Furthermore, removal of indinavir rapidly restored normal insulin-responsive glucose uptake within 30 minutes (data not shown). Amprenavir and ritonavir, also exhibited an effect comparable to that of indinavir (FIG. 1B).

Inmmunoblot Analysis of 3T3-L1 Adipocyte Fractions

Figure 2A:
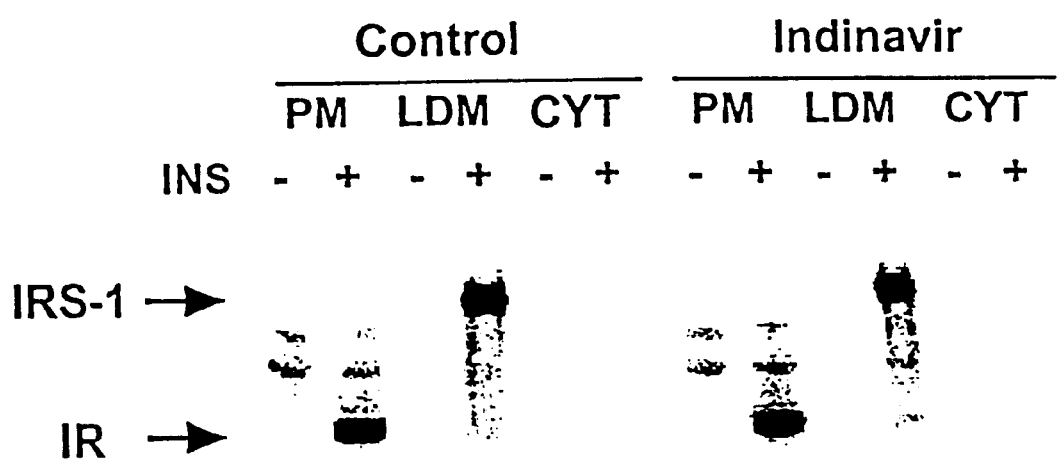
FIG. 2A. Mature 3T3-L1 adipocytes were incubated in serum-free DMEM for 4 h with or without 100 $\mu$M indinavir. Cells were further incubated for 20 min with or without 1 $\mu$M insulin, and subcellular fractions were subsequently isolate. Plasma membrane (PM), low density microsomal (LDM), and cytosolic (CYT) fractions were subjected to immunoblot analysis using anti-phosphotyrosine antibodies. The positions of the tyrosine-phosphorylated insulin receptor (IR) and insulin receptor substrate-1 (IRS-1) are indicated by arrows.

Immunoblot analysis of 3T3-L1 adipocyte subcellular fractions with anti-phosphotyrosine antibodies revealed that insulin receptor (IR) autophosphorylation and subsequent tyrosine phosphorylation of insulin receptor substrate-1 (IRS-1) occurred normally in cells exposed to indinavir (FIG. 2A). The in vivo phosphorylation status of the downstream Akt kinase was assessed using phospho-Akt specific antibodies.

Figure 2B:
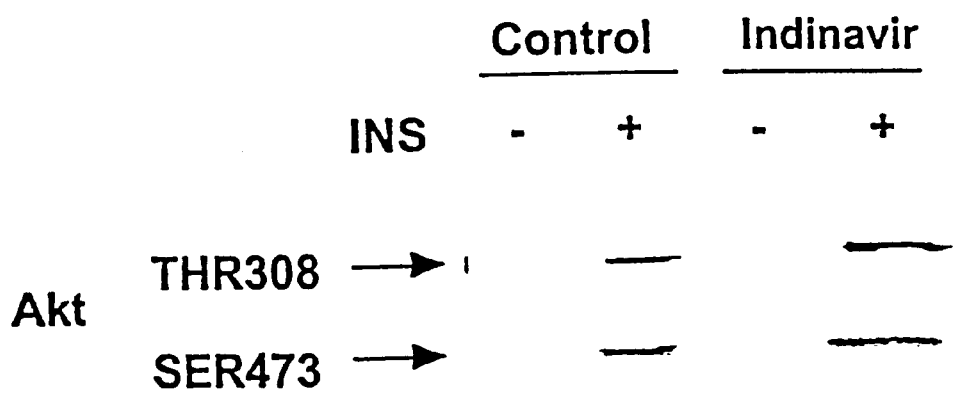
FIG. 2B. Whole cell lysates from 3T3-L1 adipocytes from samples treated as described above were subjected to immunoblot analysis using anti-phospo Akt antibodies, which recognize Akt phosphorylated on threonine 308 and serine 473.
Figure 2C:
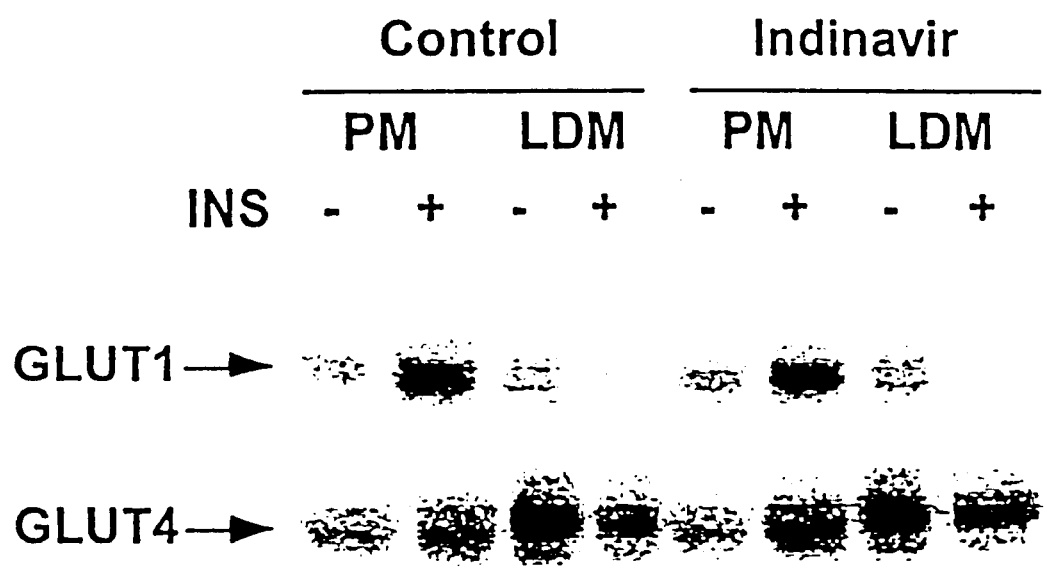
FIG. 2C. Relative Glut1 and Glut4 transporter isoform contents in the PM and LDM subcellular fractions from samples as described above were visualized by immunoblot using isoform-specific polyclonal antibodies.

Indinavir had no effect on the insulin-stimulated phosphorylation of Akt on threonine 308 or serine 473 (FIG. 2B). The glucose transporter content in the plasma membrane (PM) fractions detected by isoform-specific antibodies increased with insulin by 81% and 63% for Glut1, and by 36% and 38% for Glut4 in control and indinavir-treated cells, respectively. Concomitantly, the transporter content in the low density microsome (LDM) fractions decreased by 37% and 48% for Glut1, and by 21% and 19% for Glut4 in control and indinavir-treated cells, respectively (FIG. 2C).

Confocal Immunofluorescence Microscopy

Both control and indinavir-treated cells exhibited increased Glut1 and Glut4 staining at the plasma membrane upon stimulation with insulin. The subcellular distribution of glucose transporters was unchanged in indinavir-treated samples relative to control cells.

2-Deoxyglucose Uptake Measurements in Xenopus oocytes

Figure 3A:
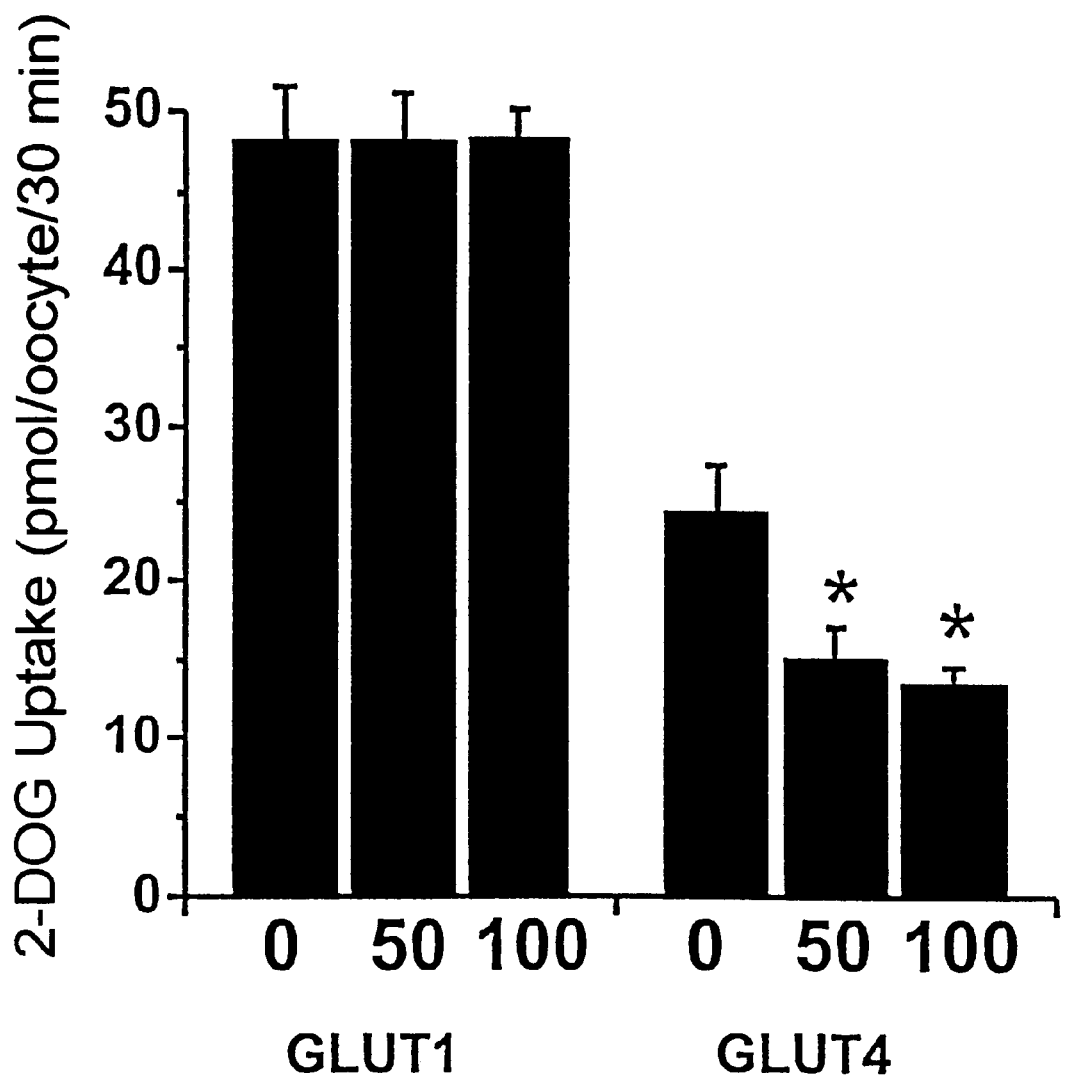
FIG. 3A. Xenopus oocytes heterologously expressing either Glut1 or Glut4 isoforms were used for [$^3$H]-2-deoxyglucose uptake measurement in Barth's Saline at 22° C. for 30 min. Immediately prior to the uptake measurement, indinavir sulfate (at the final concentrations (in $\mu$M increments) indicated on the X-axis) was added to the assay mixture. Plotted are the mean uptake from 15–20 oocytes±S.E. [* indicates p<0.01 compared with control (ANOVA with Fischer's PLSD posthoc analysis).]
Figure 3B:
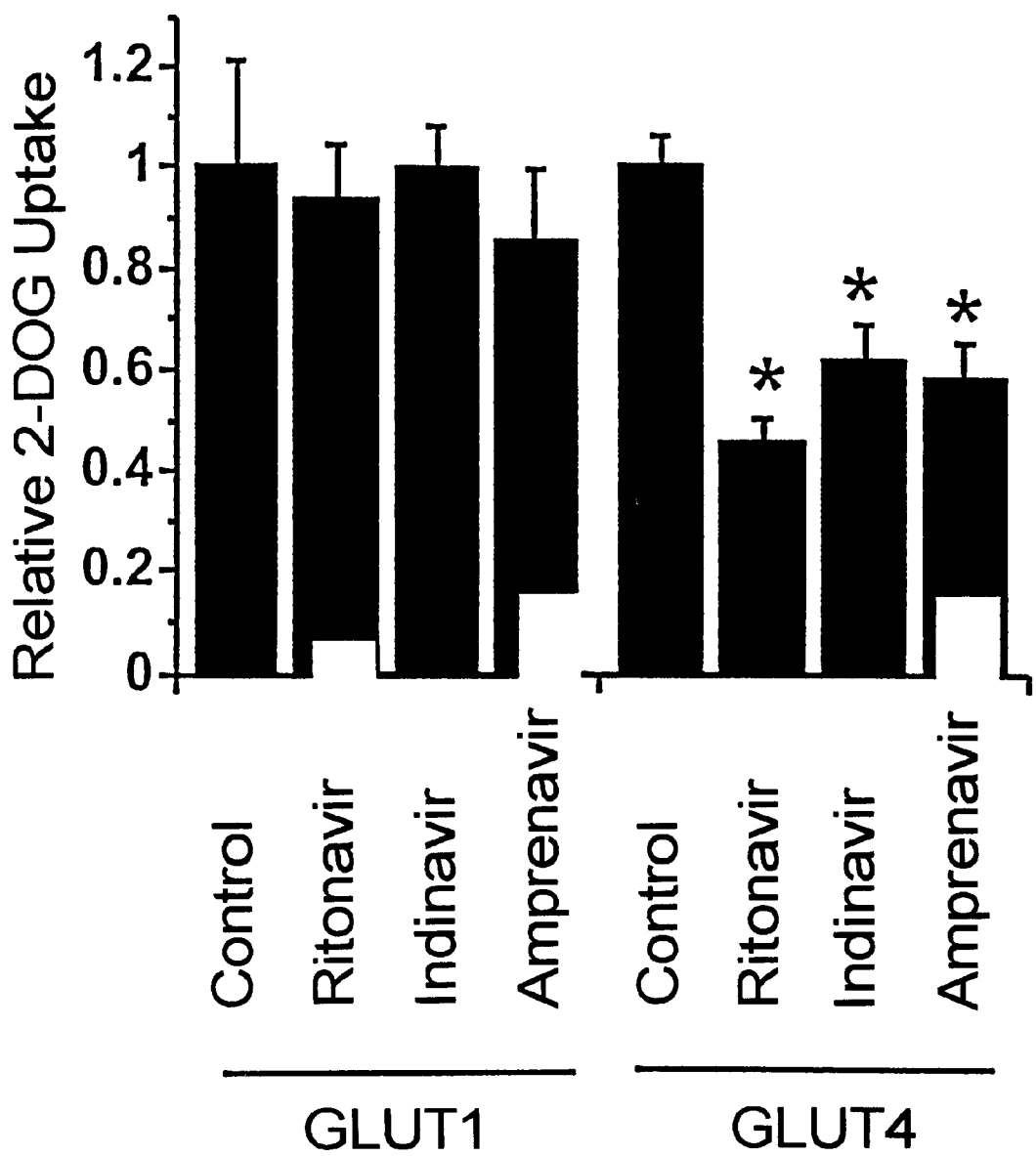
FIG. 3B. Glucose uptake in *X. laevis* oocytes as described above. Control assays are compared to those in which either ritonavir, indinavir or amprenavir at 50 μM were added to the assay mixtures immediately prior to the uptake measurements. The data are normalized to the uptake from the control oocytes which were not exposed to protease inhibitor. [* indicates p<0.0001 compared with control (ANOVA with Fischer's PLSD posthoc analysis).]

Indinavir had no effect on Glut1 activity in Xenopus oocytes. Remarkably, however, the activity of Glut4 expressed in oocytes was inhibited by 45% at the maximum dose of indinavir tested (100 $\mu$M), an effect of comparable magnitude to that observed in insulin-stimulated 3T3-L1 adipocytes (FIG. 3A). Amprenavir and ritonavir also selectively inhibited Glut4 by 54% and 42%, respectively (FIG. 3B).

Discussion

The effects of the HIV-1 protease inhibitor, indinavir, on glucose transport in 3T3-L1 adipocytes, a system that responds robustly to insulin, were initially examined. At 10 $\mu$M, which is within the physiologic range of plasma concentrations achieved in vivo in HIV patients, indinavir inhibited insulin-stimulated glucose uptake by 26% (p<0.0001). Inhibition of insulin-stimulated glucose uptake appears to be a general property of HIV-1 protease inhibitors, as two other compounds within this class, amprenavir and ritonavir, also exhibited inhibitory effects comparable to that of indinavir. As the metabolic effects of insulin require PI-3 kinase activation, the in vivo phosphorylation status of the downstream Akt kinase was assessed using phospho-Akt specific antibodies. Indinavir was found to have no effect on the insulin-stimulated phosphorylation of Akt, thus demonstrating that the PI-3 kinase signaling pathway remained intact. Insulin acutely stimulates glucose uptake in muscle and fat cells by triggering the translocation of intracellularly sequestered glucose transporters, predominantly the Glut4 transporter isoform, to the plasma membrane. 3T3-L1 adipocytes express Glut1 and Glut4, and both of these transporter isoforms appeared to translocate properly to the cell surface in response to insulin despite the presence of 100 $\mu$M indinavir. Confocal immunofluorescence microscopy of whole cells and plasma membrane A sheets also showed that the subcellular distribution of glucose transporters was unchanged in indinavir-treated samples relative to control cells. The rapid onset of inhibition observed in the glucose uptake assay (FIG. 1), in which indinavir was added to the cells after sufficient time had elapsed for the majority of the transporters to reach the plasma membrane following insulin stimulation, is consistent with indinavir acting at a site subsequent to the translocation of transporters to the plasma membrane. Additionally, the extent of inhibition of transport activity did not change if indinavir was added either before or after 20 min of insulin stimulation (data not shown).

Glut1 and Glut4 were heterologously expressed in *Xenopus laevis* oocytes by microinjection of their respective mRNA in order to test the possibility that indinavir might be directly inhibiting the intrinsic transport activity of glucose transporters. Glut1 activity was unaffected, however the transport activity of the Glut4 isoform was substantially inhibited by all three protease inhibitors tested. The data obtained in Xenopus oocytes are consistent with what is observed in 3T3-L1 adipocytes, in which basal (indinavir-resistant) and insulin-stimulated (indinavir-inhibitable) glucose uptake are largely mediated by Glut1 and Glut4, respectively. From the data presented, it is concluded that HIV protease inhibitors unexpectedly act as potent, isoform-specific inhibitors of the transport function of the Glut4 glucose transporter.

This is the first demonstration that pharmacologic manipulation of glucose transport is feasible in a selective manner. An agent that can reversibly induce an insulin resistant state would be a very useful tool in developing model systems that mimic type 2 diabetes. Glut4 is predominantly expressed in tissues responsible for the bulk of whole body glucose disposal (skeletal/cardiac muscle and fat) and is believed to be the principal transporter isoform mediating insulin-stimulated glucose uptake at these sites. As glucose transport is the rate-limiting step for whole body glucose disposal in rodents and in humans, the inhibitory effect of antiretroviral protease inhibitors on Glut4 is therefore likely to be the direct cause of insulin resistance observed in HIV patients receiving this class of drugs.

In predisposed individuals, diabetes can result after pancreatic b cells fail to compensate for the insulin resistance. A recent clinical study employing a longitudinal design comparing fasting glucose and insulin levels before and after administration of protease inhibitor therapy demonstrated that insulin resistance is apparent after a relatively short period of time (an average of 3–4 months between measurements) before significant changes in body weight and fat distribution occur.

The fact that insulin resistance appears to precede the manifestation of lipodystrophy is consistent with our hypothesis that indinavir directly causes insulin resistance through its effect on Glut4, rather than insulin resistance developing secondarily to the lipodystrophy.

It is possible that insulin resistance occurs much earlier than reported thus far, perhaps even immediately upon initiation of protease inhibitor therapy. Moreover, if this hypothesis is correct, insulin resistance should be maximal when in vivo protease inhibitor concentrations are maximal. Thus, depending on the dosing regimen and the pharmacokinetic characteristic of the protease inhibitor used, simple measurements of fasting glucose and insulin levels may be underestimating the true extent of insulin resistance that actually occurs.

A 'knockout' mouse that lacks Glut4 is insulin resistant, and interestingly, almost devoid of fat tissue. Thus, Glut4 activity per se may somehow be required for adipogenesis. If this is true, the protease inhibitor's direct effect on Glut4 may account for the clinically observed lipodystrophy in addition to the insulin resistance.

Recent reports that HIV protease inhibitors interfere with adipogenesis in cultured cell models do not contradict this hypothesis. HIV patients treated with protease inhibitors show a characteristic loss of adipose tissues at peripheral sites as opposed to the abdomen. One can speculate that peripheral adipocytes preferentially synthesize lipid de novo from blood glucose, whereas abdominal adipocytes may obtain their lipid primarily from circulating triglycerides.

As antiretroviral protease inhibitors play a vital role in prolonging the life span of HIV patients and are often administered over an extended period of time, the metabolic side effects and their chronic or acute consequences are likely to be more prevalent in the future. Further drug development is necessary in order to design new compounds that maintain the efficacy in the management of HIV infection, but that also minimize the detrimental effect on the glucose transport system observed in this study.

EXAMPLE 2

In vivo Verification of the Mechanism of Insulin Resistance Caused by HIV Protease Inhibitor Therapy and Application of Same Materials and Methods Male Wistar rats (Charles River Corp) weighing between 250–400 g were used for all experiments described below. Glucose measurements were made using a Glucometer Elite Glucometer (Bayer Corporation, Diagnostics Division, Tarrytown, N.Y.). Protease inhibitor used was Indinavir (Merck). Jugular vein and carotid artery catheters were fabricated using microrenathane tubing (Braintree Scientific) for venous catheters and PE50 tubing (Becton Dickenson) for arterial catheters. Catheters were inserted surgically under methohexital (Jones Pharma Inc, St. Louis, Mo.) anesthesia. Humulin R insulin (Eli Lilly, Indianapolis, Ind.) was used where indicated.

Effect of Acute Indinavir Administration on Glucose Tolerance in vivo

Figure 4A:
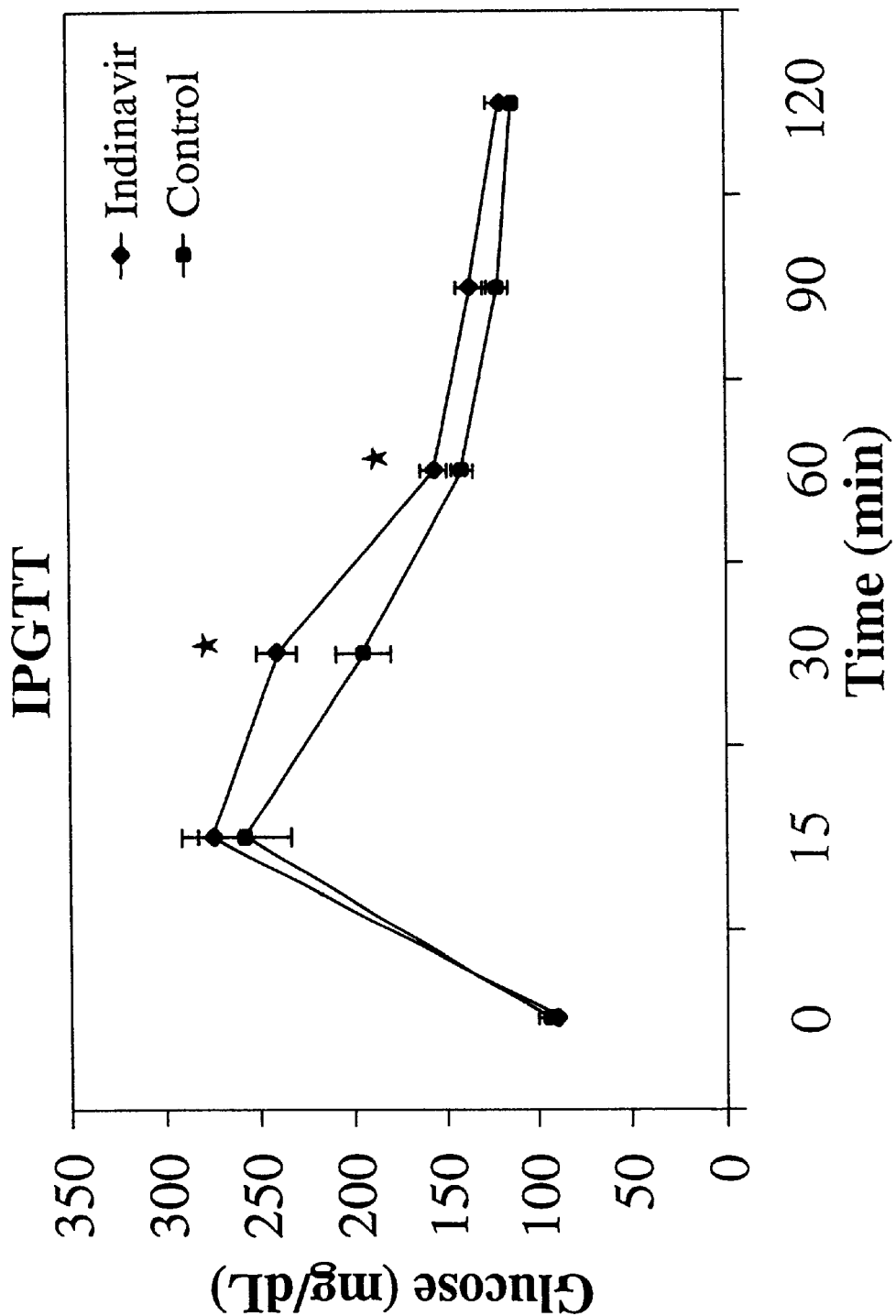
FIG. 4A. Following a 12 hour overnight fast, male Wistar rats weighing 250–400 grams were given a single intraperitoneal dose of 50% dextrose (2 gm/kg) together with indinavir (10 mg/kg) or water. From samples of peripheral venous blood, plasma glucose levels were measured using a Glucometer Elite glucometer. Each data point represents the mean±SEM values from 8–9 rats.

To determine whether protease inhibitors acutely affect insulin sensitivity in vivo, the following experiments was conducted: Following a 12 hour fast, male Wistar rats were given a single intraperitoneal injection of 50% dextrose, in water, to a dose of 2 g/kg, together with either Indinavir (10 mg/kg) or water (for Control animals). Plasma glucose levels were measured in peripheral venous blood at times (t)=0, 15, 30, 60, 90, and 120 min after injection. The results from 8–9 animals were averaged for each data point. Results are shown in FIG. 4a. By t=30 min, blood glucose concentrations were significantly elevated (p<0.05) in indinavir-treated animals (241±11 mg/dl) relative to those of control animals (195±15 mg/dl).

Figure 4B:
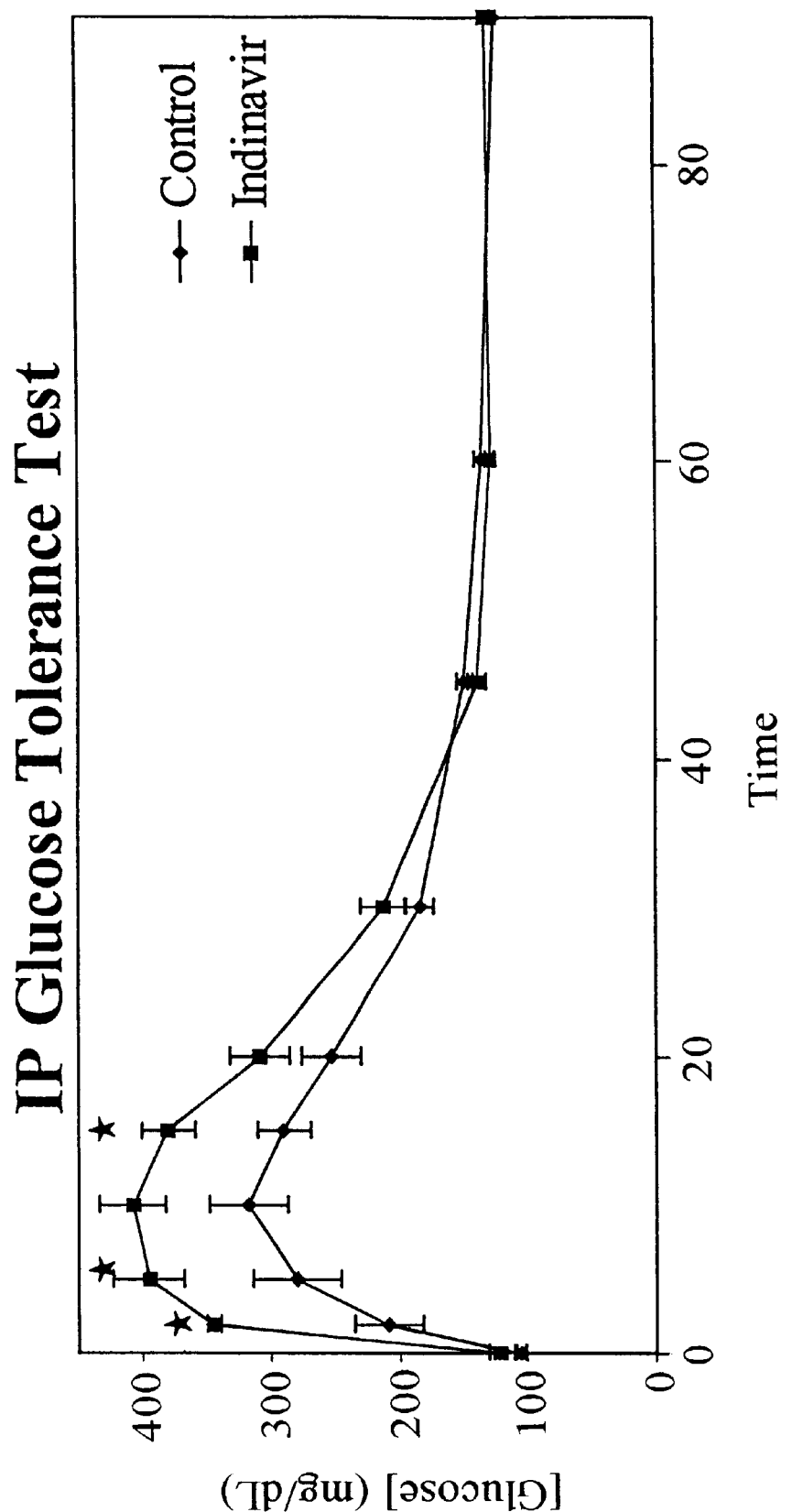
FIG. 4B: A jugular venous catheter was inserted, at least 4 days prior to each experiment, into 200–300 gm male Wistar rats under methohexital anesthesia. Following a 12 hour fast, rats were injected with indinavir (15 mg/kg in normal saline) or saline through the venous catheter 5 minutes prior to intraperitoneal injection of 50% Dextrose (2 gm/kg). Plasma glucose levels were measured from blood sampled from the venous catheters. Values represent the mean±SEM from 4–5 rats. [* indicates P<0.05.]

To determine even earlier effects of indinavir on in vivo glucose tolerance, at least 4 days prior to each experiment catheters were inserted, under methohexital anesthesia, into the jugular veins of 200–300 gram male Wistar rats. Indinavir (15 mg/kg) was injected intravenously 5 minutes prior to the intraperitoneal injection of glucose (2 gm/kg). Blood was withdrawn via the venous catheter at t=0, 2, 5, 10, 15, 30, 60, 90 and 120 min after glucose injection and plasma glucose concentrations were determined. Results are shown in FIG. 4b. Under these conditions, an even greater elevation in plasma glucose concentrations was observed following indinavir treatment. Peak glucose concentrations were 407±25 mg/dL in indinavir-treated animals compared to 311±30 mg/dL in water-treated controls.

EXAMPLE 3

Figure 5B:
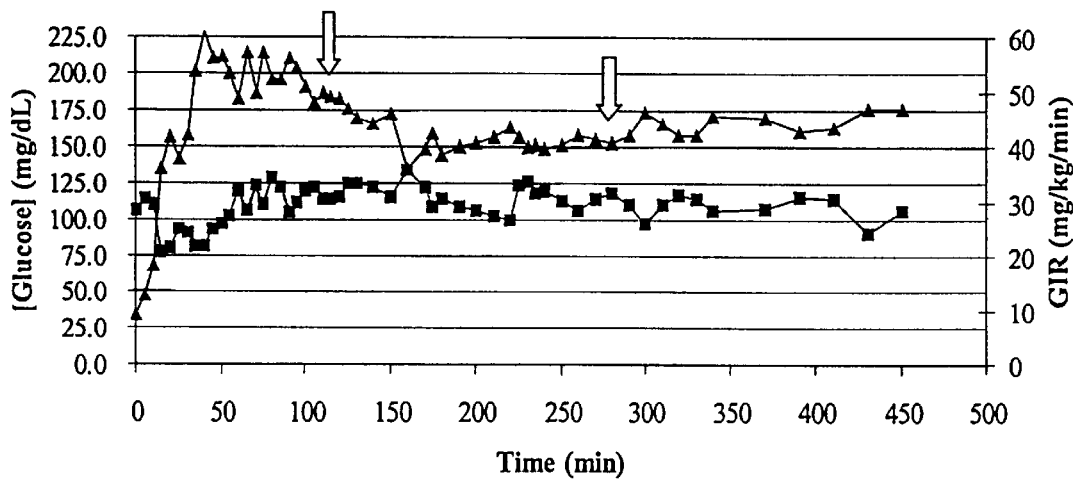

Effect of Acute Intravenous Administration of Indinavir on Peripheral Insulin Sensitivity in vivo Peripheral insulin sensitivity in rats was assessed by the euglycemic hyperinsulinemic clamp technique. Venous and arterial catheters were surgically inserted into the animals under anesthesia. At least 4 d prior to the initiation of experimental treatments catheters were inserted into both jugular vein and carotid artery locations. Following a 12 hour fast, animals were infused with insulin (40 mU/kg/min) and 50% dextrose in water through the venous catheter. Blood was sampled every 5–10 min through the arterial catheter for serum glucose determinations. The rate of glucose infusion (Glucose Infusion Rate, GIR) was adjusted as necessary to maintain serum glucose at 100–110 mg/dl (FIGS. 5A, 5B, 5C).

After obtaining a stable GIR (120 min), a water infusion containing indinavir at 0.0, 0.3, or 0.5 mg/kg/min was started through the venous catheter. The indinavir-containing infusion was discontinued after approximately 120 minutes and the euglycemic infusion was continued for approximately another 4 h.

Figure 5C:
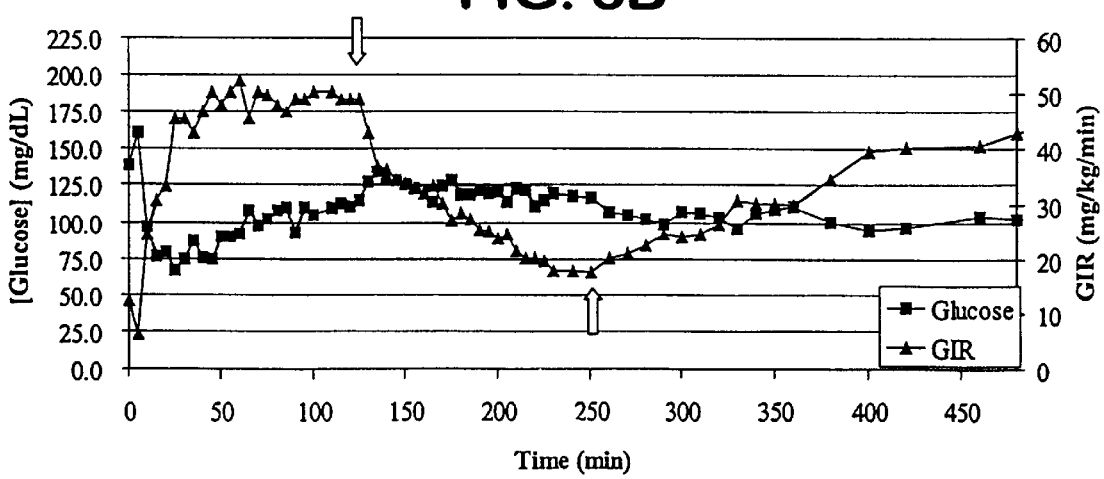

A 50% decrease in the GIR required to maintain euglycemia was observed within 90 minutes after starting the intravenous infusion of indinavir at a rate of 0.5 mg/kg/min (FIG. 5C). At an indinavir infusion rate of 0.3 mg/kg/min, a 20% decrease in GIR was observed (FIG. 5B).

The reduction in the GIR required to maintain euglycemia reflects a decrease in the rate at which glucose was being removed from the serum, thereby reducing the need for incoming glucose to maintain a homeostatic concentration of serum glucose. Insulin sensitivity was restored to baseline within 4 h after stopping the indinavir infusion, as reflected by the increase in GIR (FIGS. 5A, 5B, 5C)

In a separate set of experiments, the infusion of indinavir or water was started 30 minutes prior to the start of euglycemic hyperinsulinemic clamp procedure. Insulin sensitivity was assessed by the average glucose infusion rate required to maintain euglycemia after equilibrium had been established. Statistically significant reductions in peripheral insulin sensitivity (p<0.05) were observed both with an indinavir infusion rate of 0.3 mg/kg/min (15% reduction) and 0.5 mg/kg/min (40% reduction) compared with controls (FIG. 6).

These data demonstrate that antiretroviral protease inhibitors cause acute and reversible changes in whole body glucose homeostasis and selective inhibition of GLUT4 glucose transporter isoform. The data also support the contribution of the GLUT4 isoform inhibition to the development of insulin resistance in patients treated with protease inhibitors.

The present invention is not limited in any manner to the embodiments described and exemplified above. It is capable of variation and modification in accordance with the scope of the appended claims.

I claim:

1. A method for screening an antiretroviral protease inhibitor for a metabolic side-effect on glucose transport, the method comprising the steps of:
   a) providing a reaction medium comprising one or more glucose transporters in a membrane system through which the glucose transporters transport a glucose compound;
   b) adding to the reaction medium a detectable form of the glucose compound;
   c) adding to the reaction medium the protease inhibitor to be screened;
   d) determining activity of the glucose transporter by measuring an amount of the glucose compound transported by the glucose transporter; and
   e) quantifying the metabolic side-effects of the protease inhibitor screened as a function of the activity of the glucose transporter in the presence the protease inhibitor as compared with the activity of the glucose transporter in the absence of the protease inhibitor.

2. The method of claim 1 wherein the glucose transporter is a Glut4 isoform.

3. The method of claim 1 wherein the membrane system is selected from the group consisting of cells, cell membranes, cell ghosts, erythrocyte ghosts, membrane-derived vesicles, lipid-containing vesicles, artificial membranes, lipid-containing monolayers, black lipid membranes, reconstituted membranes, hybrid bilayer membranes, supported bilayer membranes, phospholipid-containing membranes and lipid-containing micelles.

4. The method of claim 3 wherein the membrane system comprises cells and the cells are selected from the group consisting of adipocytes, oocytes, kidney cells, cardiac cells, skeletal muscle cells, liver cells, neuronal cells, brain cells, Xenopus cells, *Escherichia coli, Saccharomyces cerevisiae,* insect cells, mouse cells, rat cells, chimpanzee cells, human cells, tumor cells, cancerous cells, transformed cells, and genetically engineered cells.

5. The method of claim 3, wherein the membrane system comprises cells and the cells contain one or more expressible nucleic acid molecules encoding the one or more glucose transporters.

6. The method of claim 5, wherein the nucleic acid molecule encoding the glucose transporter is a heterologous nucleic acid molecule to the cells.

7. The method of claim 5 wherein the cells have a substantially negligible basal level of glucose transport other than the glucose transport provided by the heterologous glucose transporter.

8. The method of claim 5 wherein the expression of the glucose transporter is a stable characteristic of the cell.

9. The method of claim 8 wherein the nucleic acid encoding the glucose transporter is integrated into the chromosome or is contained within an extrachromosomal element.

10. The method of claim 5 wherein the expression of the glucose transporter is a transient characteristic of the cell.

11. The method of claim 10 wherein the nucleic acid is an mRNA which is microinjected into the cell.

12. The method of claim 1, which further comprises a step of adding a glucose transport-altering substance to the reaction medium.

13. The method of claim 12 wherein the membrane system comprises cells and the glucose transport altering substance has the biological activity of a hormone.

14. The method of claim 13 wherein the hormone is insulin.

15. The method of claim 1 wherein the protease inhibitor is added to the reaction medium at any time during the assay.

16. A kit for use in screening protease inhibitors for metabolic side effects on glucose transport, the kit comprising one or more components selected from the group consisting of a reaction vessel, a cell line capable of expressing one or more glucose transporters, a membrane system containing one or more glucose transporters, one or more nucleic acid sequences encoding a glucose transporter, one or more mRNA sequences encoding a glucose transporter for transient expression, a detectable glucose compound, a standardized protease inhibitor, a control glucose transport inhibitor, glucose transport altering substances, control cells, standards for validating the assay, detailed instructions, quality control certifications, disposable labware, and disposable personnel protective items.

17. A method of developing improved therapeutic compounds safe and effective in managing an infection with a retrovirus, the method comprising the steps of:

a) identifying a therapeutic compound of interest;
b) testing the compound with the following steps;
   1) determining that the compound inhibits the aspartyl protease of the retrovirus;
   2) using the compound as a protease inhibitor in the method of claim 1; and
   3) assessing the compound for inhibition of glucose transport; and
c) selecting compounds which inhibit the aspartyl protease and which do not inhibit glucose transport.

18. A cell-free assay for determining if a selected glucose transporter physically associates with a selected protease inhibitor, the method comprising the steps of:

a) labeling the glucose transporter or the protease inhibitor, or both, with a detectable label, wherein a measurable feature of the detectable label changes if the glucose transporter physically interacts with the protease inhibitor;
b) adding the glucose transporter and the protease inhibitor to a reaction medium under conditions enabling physical association, if any, between the glucose transporter and the protease inhibitor; and
c) measuring a change, if any, in the measurable feature of the detectable label, the change being indicative that the glucose transporter and the protease inhibitor physically interact.

19. The assay of claim 18, wherein the glucose transporter is a Glut4 isoform.

20. The assay of claim 18, wherein the physical interaction is selected from the group consisting of hydrophobic interactions, hydrophilic interactions, covalent interactions, Van der Waal's interactions, ionic interactions.

21. The assay of claim 20, wherein the physical interaction results in occlusion of an active site of the glucose transporter or protease inhibitor or blockage of the glucose transporter's glucose translocation channel.

22. The assay of claim 18 wherein the detectable label is selected from the group consisting of isotopic labels, fluorescent labels, and photolabile labels.

23. The assay of claims 18 wherein the measurable change in the detectable label is quenching of a signal produced by the detectable label.

24. The assay of claim 18 wherein the measurable change in the detectable label is a change in a spectrophotometric feature of the detectable label.

25. The assay of claim 18 wherein the glucose transporter is soluble in the reaction medium.

26. The assay of claim 18 wherein the glucose transporter is contained within a membrane system.

27. A method for screening therapeutic test compounds for their ability to alleviate insulin resistance, the method comprising the steps of:

a) providing a reaction medium comprising:
   i) cells that produce one or more glucose transporters;
   ii) a quantity of an inhibitor of retroviral protease that reversibly inhibits insulin-dependent glucose transport of the transporter;
   iii) a quantity of insulin; and
   iv) a glucose compound;
b) measuring the amount of the glucose compound transported into the cells under preestablished conditions for a preestablished time period;
c) adding the test compound to the reaction medium;
d) measuring the amount of the glucose compound transported into the cells under preestablished conditions for a preestablished time period; and e) determining the difference between the amount of glucose transported into the cells after addition of the test compound and the amount of glucose transported into the cells before addition of the test compound, an increase in the amount of glucose transported into the cells after addition of the test compound being indicative that the test compound is capable of reversing the inhibition of the insulin-dependent glucose transport caused by the protease inhibitor.

28. The method of claim 27 wherein the quantity of insulin is substituted with a quantity of a glucose transport-altering substance.

* * * * *